United States Patent
Boissier et al.

(12) 
(10) Patent No.: US 6,596,315 B1
(45) Date of Patent: Jul. 22, 2003

(54) METHOD OF PRODUCING DRUG PARTICLES

(75) Inventors: Catherine Boissier, Göteborg (SE); Anne Mari Juppo, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/486,688

(22) PCT Filed: Nov. 22, 1999

(86) PCT No.: PCT/SE99/02152

§ 371 (c)(1),
(2), (4) Date: Mar. 1, 2000

(87) PCT Pub. No.: WO00/30612

PCT Pub. Date: Jun. 2, 2000

(30) Foreign Application Priority Data

Nov. 23, 1998 (SE) ............................................. 9804003

(51) Int. Cl.$^7$ ................................................. A61K 9/14
(52) U.S. Cl. ....................................... 424/489; 424/400
(58) Field of Search ............................... 424/489; 514/2

(56) References Cited

U.S. PATENT DOCUMENTS 5,043,280 A     8/1991   Fischer et al. ............ 435/235.1
5,770,559 A  *  6/1998   Manning et al. ................ 514/2

FOREIGN PATENT DOCUMENTS

| WO | 9003782 | | 4/1990 | | |
| WO | WO 90/03782 | * | 4/1990 | ............ | A61K/9/14 |
| WO | 9600610 | | 1/1996 | | |
| WO | 9619198 | | 6/1996 | | |
| WO | WO 96/19198 | * | 6/1996 | ............ | A61K/9/12 |
| WO | 9714407 | | 4/1997 | | |
| WO | WO 97/14407 | * | 4/1997 | ............ | A61K/9/14 |
| WO | 9828294 | | 7/1998 | | |

OTHER PUBLICATIONS

Sigma Chemical Company Catalogue, 1992, pp. 817 and 964.*
"Evaluation of Supercritical Fluid Extraction in the Pharmaceutical Industry", Larson, Karen A. and King, Michael L., *Biotechnology Progress*, (1986), vol. 2, No. 2, pp. 73–82.
*Langmuir*, Yee, Geary G., Fulton, John L., Smith, Richard D., (1992) vol. 8, No. 2 pp. 377–384.
*Journal of the American Chemical Society*, Fulton, John L., Yee, Geary G., Smith, Richard D., (1991) vol. 113, No. 22, pp. 8327–8334.
"Finely–Divided Powers by Carrier Solution Injection into a New or Supercritical Fluid", Schmitt, William J., Salada, Michael C., Shook, Gary G., Speaker III, Stanley M., *AIChE Journal*, (1995), vol. 41, No. 11, pp. 2476–2486.
"Precipitation of Microsize Organic Particles from Supercritical Fluids", Chang, C.J. and Randolph, A. D., *AIChE Journal*, (1989), vol. 35, No. 11, pp. 1876–1881.
*Journal of Aerosol Science*, Tom, W. Jean and Debenedetti, Pablo, G., (1990), pp. 555–584.
"Supercritical Fluid Science and Technology", ACS Symposium Series 406, Johnston, Keith P., Penninger, J.M.L., (1988), Chapter 22, pp. 334–354.
"Application of supercritical fluid for the production of sustained delivery devices", Debenedetti, Pablo G., Tom, Jean , W. Tom, Yeo, Sang–Do, Lim, Gio–Bin, *Journal of Controlled Release*, (1993), pp. 27–44.

* cited by examiner

Primary Examiner—Thurman K. Page
Assistant Examiner—Robert M. Joynes
(74) *Attorney, Agent, or Firm*—White & Case LLP

(57) ABSTRACT

A method of preparing drug particles of a substance which are susceptible to degradation by the use of a fluid gas technique.

7 Claims, No Drawings

METHOD OF PRODUCING DRUG PARTICLES

FIELD OF THE INVENTION

The present invention relates to a method for the production of drug particles. More specifically, the invention relates to a method for the production of drug particles having minimal amount of degradation products when obtained by a fluid gas technique process. The invention also relates to such particles when obtained by the method of the invention.

BACKGROUND OF THE INVENTION

The strategy for the pharmaceutical formulation work of a given drug depends on different factors. Ultimately, these factors emanate from 1) the therapeutic needs, 2) the physical chemical properties of the drugs, and 3) the influence from the biological environment where the formulation will release its contents. Thus, both technical and biopharmaceutical considerations will contribute to a successful therapy.

However, improved drug administration will also be achieved by development of microparticles. The particle size of a poorly soluble drug is often the key role to a beneficial bioavailability. In this development, particles having a high content of active substance, with narrow particle size distribution are desired. These requirements of the micronization process is not always fulfilled, using conventional size-reduction techniques, such as traditional milling or grinding. When subjected to conventional micronization techniques, solids, sensitive to thermal degradation or chemical reactions may be degraded.

The use of supercritical fluids as transport media in the formation of fine powders is a known micronization technique (Krukonis V, AIChE meeting, Paper 140f, November (1984) San Francisco; King M L, Larson K A, Biotechnology Progress, vol. 2, No. 2 (1986) 73–82). One of the advantages using a supercritical fluid as a solvent is that organic solvents can be avoided. Generally, when using supercritical techniques, there are less residual solvents in the produced powder. The operating temperatures are usually low, compared to conventional techniques and the particle size of the produced powder is small, having a narrow distribution. This results in smaller dose variations, when using these microparticles in a pharmaceutical formulation.

There are several techniques today that uses the properties of a supercritical fluid to produce particles. This has been reported in articles which are presented in the prior art section.

Supercritical fluids are generally considered to be chemically inert. This is crucial in the process of producing particles, using supercritical fluid crystallisation techniques. Still, there are some differences among different supercritical fluids in their interaction with other compounds (Prauznitz J M et al., Molecular Thermodynamics of fluid-phase equilibria, $2^{nd}$ Ed. (1986) Prentice-Hall Inc., Englewood Cliffs, N. J.; McHugh M, Krukonis V, Supercritical fluid extraction, $2^{nd}$ Ed. (1994) Chap. 5, Butterworth-Heinemann).

In supercritical fluid technology, the most commonly used fluid is carbon dioxide. Carbon dioxide may induce undesirable interaction with other components used in the process. It is in place to emphasize that a fluid gas (i.e material in its supercritical and near supercritical state as well as compressed gases), such as carbon dioxide, fluorocarbons, chlorocarbons, fluorochlorocarbons, etc., or mixtures thereof, may interact with any components used in the process, such as solvent(s) or substance(s), which may cause degradation of the final product.

A substance may have water included in the crystal lattice. Using supercritical fluid technology, both substance and water are then needed in the process to get the right crystal modification of the product. Water may produce acidic compound(s) when interacting with for instance carbon dioxide, sulfur dioxide, nitrogen oxide, and sulfur hexafluoride. These acid compounds may cause degradation of the substance(s) to be precipitated.

In the presence of an oxidizing agent, such as carbon dioxide (Chang C J, Randolph A D, AIChE Journal., vol. 35, No. 11 (1989) 1876–1882), alcohols may contribute to acidic conditions in an equilibrium reaction.

A fluid gas dissolved in a solvent may produce acidic conditions. Fluid gas as producing acidic conditions are for instance carbon dioxide, sulfur dioxide, nitrogen oxide, sulfur hexafluoride, fluorocarbons, chlorocarbons, and fluorochlorocarbons. Solvent producing acidic conditions are for instance alcohols, and water.

PRIOR ART

There are several techniques used today which are based on supercritical technology. One is known as rapid expansion of supercritical solutions (RESS) and another is known as gas antisolvent precipitation (GAS). In the GAS technique a substance of interest is dissolved in a conventional solvent, whereafter a supercritical fluid such as carbon dioxide is introduced into the solution, leading to rapid expansion of the volume of the solution. As a result, the solvent power decreases dramatically over a short period of time, leading to nucleation and precipitation of particles, [Gallager et al., ACS Symposium series 406, Chap. 22 (1989) 334–354; Tom J W, Debenedetti P G, J. of Aerosol Sci., 22 (1991) 555–584; Debenedetti P G et al., J. Controlled Release, 24 (1993) 27–44; WO 90/03782]. A modification of the GAS process has been developed (WO 95/01221 and WO 96/00610) called the SEDS (solution enhanced dispersion by supercritical fluid) process, which uses the concept of co-introducing a supercritical fluid and a substance in solution or suspension into a particle formation vessel.

Schmitt et al. (Schmitt et al., AIChE Journal, 41 (1995) 2476–2486) describes the use of carbon dioxide and ethane as a supercritical fluid. By injecting a solute solution into an agitated volume of supercritical or near supercritical fluid, rapid crystallisation is reported to be obtained.

Different interactions using different supercritical fluids has been reported in articles: Chang and Randolph (Chang C J, Randolph A D, AIChE J., vol. 35, No. 11 (1989), 1876–1882) who describes the dissolution of β-carotene in supercritical carbon dioxide, supercritical ethane and supercritical ethylene. When using supercritical carbon dioxide as solvent, β-carotene-related epoxide was produced (RESS technique).

EP 322 687 discloses a process wherein a fluid gas is used to obtain a substance/carrier formulation.

Fulton et al. (Fulton J L, Yee G G, Smith R D, J. Am. Chem. Soc., 113 (1991) 8327–8334; Fulton J L, Yee G G, Smith R D, Langmuir, 8 (1992) 337–384) measured the degree of intermolecular hydrogen bonding between solute molecules in different supercritical fluids and in liquid heptane. These articles describes interactions between different supercritical fluids and solute molecules.

WO 97/14407 discloses the use of supercritical ethane for beta-carotene in rapid expansion from supercritical solution.

None of the documents mentioned above discloses use a specific supercritical fluid to protect from degradation a acid labile substance in hydrate form, when applied to a supercritical technique process.

DISCLOSURE OF THE INVENTION

It has now surprisingly been found that, in a fluid gas technique process, an acid labile substance being in hydrate form can be obtained without substantial degradation of the substance.

The novel method according to the invention is based on the finding that by using specific fluid gases in the process, substances which are acid labile and in hydrate form are insignificantly influenced by the process. The result is particles having small amount of degradation products.

An object of the invention is thus to provide a method for preparing drug particles of substances, which are acid labile and in hydrate form and which method does not substantially negatively influence the substance applied to the method.

A further object of the invention is to provide the drug particles of substances, which are acid labile and in hydrate form by use of the method of the invention.

Substances on which the method according to the present invention could be applied are acid labile substances, substances containing crystal water, etc.

An acid labile substance is defined as a substance that is degraded when exposed to an acidic environment.

An acid labile substance is defined in the present specification as a substance that generates degradation products 0.2% or more of the initial weight of the substance when applying $CO_2$ as fluid gas during processing time, typically 8–24 hours, than is generated when applying any of the fluid gases according to the invention.

The substances can be, but are not limited to pharmaceutically active substances such as: hydrates of omeprazole, omeprazole Mg, omeprazole Na (S)-omeprazole, (S)-omeprazole K (dimethanolsolvate), (S)-omeprazole Mg (S)-omeprazole Na, formoterol funarate etc.

The fluid gas techniques used for the formation of the pharmaceutical product, with the active substance(s) are antisolvent techniques such as, but not limited to, SEDS, ASES (aerosol solvent extraction system), SAS (supercritical antisolvent), GAS and PCA (precipitation with compressed fluid antisolvent).

The particular fluid gas used in the method according to the present invention is selected from the group consisting of saturated or unsaturated low molecular weight hydrocarbons, xenon, dimethyl ether and mixtures of these gases. Saturated or unsaturated low molecular weight hydrocarbons are such as having 1–6 carbon atoms, for instance ethane and propane. Particularly preferred is ethane.

The definition of fluid gas in this application includes material in its supercritical and near supercritical state as well as compressed gases.

The method according to the invention of producing particles of substances which are susceptible to degradation is characterized in that it comprises the following steps:

a) Dissolution of the substance or substances in a solvent or a mixture of solvents.

The solvents that can be used are alcohols, ethers, ketones, esters, alkanes, halides etc., or mixtures thereof. Examples of such solvents are methanol, ethanol, isopropanol, n-propanol, methylene chloride, acetone, ethylacetate, ethylether, or mixtures thereof. Also other solvents used as such or in mixtures with these above or in between can be but are not limited to water, ammonia and dimethylsulfoxide (DMSO).

Solvents such as those mentioned above can be added to the process as modifiers or co-solvents. By adding modifiers to the process the physical properties of the fluid gas is altered. For example, this may be done to alter the solubility of substance(s) or its solvent(s) in the fluid gas. If the amount of water used in the process is higher than the maximum amount to obtain a single phase system in the process, a modifier might be needed. The modifier is mixed with the fluid gas, before contacting the solution or co-introduced with the solution just before contact with the fluid gas. As modifiers or co-solvents should be mentioned alcohols, ethers, ketones, esters, alkanes, halides etc., or mixtures thereof Examples of such modifiers or co-solvents are methanol, methylene. chloride, ethylacetate, acetone or any of the others mentioned as examples of solvents above.

The substance is dissolved, dispersed and/or solubilised in a solvent, where water often is one of the components (but not necessarily). If the substance which is susceptible to degradation contains crystal water, the amount of water used as solvent is adjusted to the amount of crystal water needed to crystallise the substance, and to the solubility of water in the fluid gas.

b) Using the fluid gas technique to form the particles comprising one or more substance(s).

Relevant examples are given in the Experimental section.

The product containing the drug substance(s) according to this invention can be used for pharmaceutical purposes such as therapeutic, prophylactic and diagnostic purposes.

Formulations based on this invention can be used for different administrations routes, such as by oral, nasal, rectal, buccal, intraocular, pulmonary, transdemal, parenteral such as intravenous, subcutaneous, intramuscular or as an implantate.

The particles produced by the method of this invention can be used in pharmaceutical formulations in the form of a solid, semisolid, liquid dispersion, or solutions prepared by use of well known pharmaceutical techniques, such as blending, granulation, wet or dry milling, compaction, coating, etc. Further, the formulation may be monolithic, such as tablets, or capsules, or in the form of multiple formulations administrated in a tablet, capsule, or sachets.

EXPERIMENTAL SECTION

Material and Methods

In this section, the materials, analytical methods and preparation techniques used in the following examples are described.

Material

Omeprazole magnesium, tetrahydrate (Astra AB, Sweden), (S)-omeprazole magnesium, trihydrate (Astra AB, Sweden), formoterol fumarate, dihydrate (Astra AB, Sweden) were used as active substances. Ethanol (99.5%), methanol (99.8%), ammonia (33%), acetone (99.5%) and water were used as solvents. Carbon dioxide (food grade) and ethane (99.0%) were used as antisolvents (AGA gas AB).

Analysis of Particles
High-Perfomance Liquid Chromatography (HPLC)
Identification and quantification of degradation products were determined using HPLC technique.
The amount of degradation products was calculated from the chromatograms as area-%. Thus, 0.2% area-procent means that the amount of degradation products was 0.2% of the initial weight of the substance.
Powder X-ray Diffraction (pXRD)
The crystal characteristics of the produced powder were studied in an X-ray powder diffiactometer (Siemens D5000, Germany).
Fourier Transform-Raman (FT-Raman)
The crystal characteristics of the produced powder were studied, using FT-Raman spectroscopy (FT-Raman, PE2000, UK).
Thermogravimetric analysis (TGA)
The amount of crystal water in the produced powder was studied using TGA (Mettler-Toledo TA8000, Switzerland).

Preparation of Particles

Particles were prepared in a modified SEDS equipment (Bradford Particle Design Limited, UK) from a solution, containing substance(s).

The solution and the antisolvent were introduced into a coaxial nozzle, which was located inside a pressure vessel. Under controlled pressure and temperature conditions, the antisolvent extracts the solvent from the solution droplets. The concentration of the solute in the droplets is thereby increased, leading to rapid particle formation. The particles were collected in a vessel, while the antisolvent and the extracted solvent emerged through a back pressure regulator.

The nozzle used was a two component nozzle, with an opening of 0.2 mm in diameter. In the two component nozzle the supercritical fluid passes through the inner passage, while the solution passes through the outer passage.

EXAMPLE 1

Omeprazole Magnesium, Tetrahydrate

Omeprazole magnesium was dissolved in ethanol, in an ultrasonic bath. After dissolution, water or ammonia were slowly added to the solution. Several compositions of the omeprazole magnesium solution were used in different experiments (Table 1).

TABLE 1

Compositions of the omeprazole magnesium solution.

| Composition no. | Solution in experiments | Concentration (w/v %)* | Ethanol (99.5%) (v %) | Water (v %) | Ammonia (33%) (v %) |
|---|---|---|---|---|---|
| 1-1 | 1-1a | 1.0 | 97.0 | — | 3.0 |
| 1-1 | 1-1b | 1.0 | 97.0 | — | 3.0 |
| 1-2 | 1-2b | 1.0 | 97.0 | 3.0 | — |
| 1-3 | 1-3a | 0.625 | 98.25 | — | 1.75 |
| 1-3 | 1-3b | 0.625 | 98.25 | — | 1.75 |
| 1-4 | 1-4b | 0.625 | 98.25 | 1.75 | — |

*(w/v %) weight/volume %

The solution (several compositions) was co-introduced with the antisolvent (carbon dioxide or ethane) in the coaxial nozzle under controlled temperature and pressure (Table 2).

TABLE 2

SEDS processing of different solutions, using different antisolvents.

| Experiments | Antisolvent | Pressure (bar) | Temperature (° C.) | Flow rate antisolvent (ml/min) | Flow rate solution (ml/min) | Degradation products (a %)* |
|---|---|---|---|---|---|---|
| 1-1a | $CO_2$ | 80 | 60 | 9.0 | 0.10 | 0.5 |
| 1-1b | ethane | 80 | 60 | 9.0 | 0.10 | 0.2 |
| 1-2b | ethane | 80 | 60 | 9.0 | 0.10 | 0.2 |
| 1-3a | $CO_2$ | 100 | 65 | 7.5 | 0.15 | 0.4 |
| 1-3b | ethane | 100 | 65 | 7.5 | 0.15 | 0.2 |
| 1-4b | ethane | 100 | 65 | 7.5 | 0.15 | 0.1 |

*(a %) area %

The particles made from a solution, using ethanol and ammonia (33%) as solvents (compositions 1-1 and 1-3 in Table 1), were crystallised as omeprazole magnesium tetrahydrate, when ethane was used as antisolvent (PXRD, TGA, FT-Raman). The degradation products were 0.2 area % in sample 1-1b and 1-3b (HPLC).

When ethanol and water were used as solvents (composition 1-2 and 1-4 in Table 1), the material still crystallised as omeprazole magnesium tetrahydrate, when ethane was used as antisolvent (PXRD, TGA FT-Raman). The degradation products were 0.2 area % in 1-2b and 0.1 area % in 1-4b (HPLC).

When using carbon dioxide as antisolvent the produced particles consisted of anhydrous omeprazole (composition 1-1 and 1-3 in Table 1) (PXRD, TGA, FT-Raman). The degradation products were 0.5 area % in 1-1a and 0.4 area % in 1-3a (HPLC).

The amount of degradation products are summerized in Table 2.

The experiments clearly show that by using the method of this invention, a better product (i.e lower amount of degradation products) is obtained with ethane as anti-solvent.

EXAMPLE 2

(S)-omeprazole Magnesium, Trihydrate (S)-omeprazole magnesium was dissolved in ethanol, in an ultrasonic bath. After dissolution, water was slowly added to the solution. One composition of the s-omeprazole magnesium solution was used in the experiments (Table 3).

TABLE 3

Compositions of the (S)-omeprazole magnesium solution.

| Composition no. | Solution in experiments | Concentration (w/v %) | Ethanol (99.5%) (v %) | Water (v %) |
|---|---|---|---|---|
| 2-1 | 2-1a | 1.0 | 97.0 | 3.0 |
| 2-1 | 2-1b | 1.0 | 97.0 | 3.0 |

The solution was co-introduced with the antisolvent (carbon dioxide or ethane) in the coaxial nozzle under controlled temperature and pressure (Table 4).

TABLE 4

SEDS processing of solution, using different antisolvents.

| Experiments | Antisolvent | Pressure (bar) | Temperature (° C.) | Flow rate antisolvent (ml/min) | Flow rate solution (ml/min) | Degradation products (a %) |
|---|---|---|---|---|---|---|
| 2-1a | $CO_2$ | 150 | 45 | 9.0 | 0.1 | 2.1 |
| 2-1b | ethane | 150 | 45 | 9.0 | 0.1 | 0.3 |

The particles made from a solution, using ethanol and water as solvents, were crystallised as (S)-omeprazole magnesium hydrate, when ethane was used as antisolvent (PXRD, FT-Raman). Sample 2-1b was found to contain about 3.4 moles of hard bound water (TGA). The pattern of weight loss suggests that the sample is crystalline. The degradation products in 2-1b were 0.3 area % (HPLC).

The particles formed, using carbon dioxide as antisolvent were amorphous. The analysis shows no crystalline content in sample 2-1a (PXRD, FT-Raman). The pattern of weight of loss suggests that the sample is amorphous (TGA). The degradation products were 2.1 area % in 2-1a (HPLC).

The amount of degradation products are summerised in Table 4.

The experiments clearly show that by using the method of this invention, a better product is obtained with ethane as anti-solvent.

Example 3

Formoterol Fumarate, Dehydrate

Formoterol flimarate was dissolved in methanol, in an ultrasonic bath. After dissolution, water was slowly added to the solution. Several compositions of the formoterol fumarate solution were used in different experiments (Table 5).

TABLE 5

Compositions of the formoterol fumarat solution.

| Composition no. | Solution in experiments | Concentration (w/v %) | Methanol (99.8%) (v %) | Water (v %) |
|---|---|---|---|---|
| 3-1 | 3-1a | 2.0 | 99.0 | 1.0 |
| 3-1 | 3-1b | 2.0 | 99.0 | 1.0 |
| 3-2 | 3-2a | 2.0 | 98.0 | 2.0 |
| 3-2 | 3-2b | 2.0 | 98.0 | 2.0 |

The solution (several compositions) was co-introduced with the antisolvent (carbon dioxide or ethane) in the coaxial nozzle under controlled temperature and pressure (Table 6).

TABLE 6

SEDS processing of different solutions, using different antisolvents.

| Experiments | Antisolvent | Pressure (bar) | Temperature (° C.) | Flow rate antisolvent (ml/min) | Flow rate solution (ml/min) | Degradation product a (w %) |
|---|---|---|---|---|---|---|
| 3-1a | $CO_2$ | 80 | 40 | 9.0 | 0.3 | 0.26 |
| 3-1b | ethane | 80 | 40 | 9.0 | 0.3 | 0.07 |
| 3-2a | $CO_2$ | 100 | 45 | 10.0 | 0.3 | 0.22 |
| 3-2b | ethane | 100 | 45 | 10.0 | 0.3 | 0.11 |

The particles made from a solution, using methanol and water as solvents (composition 3-1 and 3-2 in Table 5), were crystallised as formoterol fumarate dihydrate, when ethane was used as antisolvent (PXRD, TGA). The degradation products were 0.07 weight % in 3-1b and 0.11 weight % in 3-2b (HPLC).

When using carbon dioxide as antisolvent, the produced particles in experiment 3-1a contained amorphous formoterol fumarate (composition 3-1 in Table 5). Experiment 3-2a resulted in a mixture of formoterol fumarate dihydrate and formoterol fumarate anhydrate B (composition 3-2 in Table 5) (pXRD, TGA). The degradation products were 0.26 weight % in 3-1a and 0.22 weight % in 3-2a (HPLC).

The amount of degradation products are summarized in Table 6.

The experiments clearly show that by using the method of this invention, a better product is obtained with ethane as anti-solvent.

What is claimed is:

1. A method of preparing drug particles of an acid labile substance in hydrate form, wherein the method is a fluid gas technique process, comprising the steps of:
   a) dissolving an acid labile substance hydrate in a solvent of mixture of solvents; and
   b) applying a fluid gas to the solvent containing the dissolved acid labile substance to obtain particles comprising the acid labile substance in hydrate form without substantial degradation of the acid labile substance, wherein the fluid gas is selected from the group consisting of low molecular weight saturated and unsaturated hydrocarbons, xenon, dimethyl ether and mixtures thereof.

2. The method according to claim 1 wherein the acid-labile substance is a hydrate of omeprazole, or its magnesium or sodium salt.

3. The method according to claim 1 wherein the acid-labile substance is a hydrate of (S)-omeprazole, or its magnesium, sodium or potassium salt.

4. The method according to claim 1 wherein the acid-labile substance is a hydrate of formoterol fumarate.

5. The method according to any of the preceding claims wherein the fluid gas is a saturated or unsaturated hydrocarbon having from 1 to 6 carbon atoms.

6. The method according to claim 5 wherein the hydrocarbon is ethane.

7. The drug particle of an acid labile substance in hydrate form prepared by the method of claim 1.

* * * * *